United States Patent [19]

Teach

[11] 4,110,105
[45] Aug. 29, 1978

[54] AROMATIC N-SUBSTITUTED HALO-SUBSTITUTED-2-PYRROLIDINONES AND THEIR UTILITY AS HERBICIDES

[75] Inventor: Eugene G. Teach, El Cerrito, Calif.

[73] Assignee: Stauffer Chemical Company, Westport, Conn.

[21] Appl. No.: 647,963

[22] Filed: Jan. 9, 1976

Related U.S. Application Data

[63] Continuation-in-part of Ser. No. 563,279, Mar. 28, 1975, abandoned.

[51] Int. Cl.$^2$ .................... C07D 207/26; A01N 9/22; A01N 9/12; A01N 9/14
[52] U.S. Cl. .................. 71/95; 260/326.5 S; 260/326.5 FL; 260/326.5 SF; 260/558 P; 260/558 S; 260/559 R; 260/574; 260/577
[58] Field of Search ................. 71/95; 260/326.5 SF, 260/326.5 S, 326.5 FL

[56] References Cited

U.S. PATENT DOCUMENTS 3,488,732  7/1970  Heiba .......................... 260/343.6

OTHER PUBLICATIONS

Adcock et al., J. Amer. Chem. Soc. 96, 1595 (1974).

Primary Examiner—Donald G. Daus
Assistant Examiner—Mark L. Berch
Attorney, Agent, or Firm—Harry A. Pacini

[57] ABSTRACT

Monocyclic aromatic N-substituted halo-2-pyrrolidinones having the formula

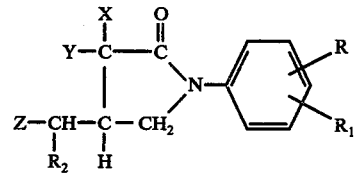

in which X is hydrogen, chlorine or methyl; Y is hydrogen, chlorine or bromine, Z is chlorine or bromine; $R_2$ is alkyl or hydrogen; R is hydrogen, alkyl, acetyl, chlorine, bromine, fluorine, iodine, trifluoromethyl, nitro, cyano, alkoxy, alkylthio, alkylsulfinyl, alkylsulfonyl, trifluoromethylthio, trifluoromethylsulfinyl, trifluoromethylsulfonyl, pentafluoropropionamido, or 3-methylureido; and $R_1$ is hydrogen, alkyl, chlorine or trifluoromethyl. The compounds of this invention are prepared by a novel process and are useful as herbicides.

98 Claims, No Drawings

AROMATIC N-SUBSTITUTED HALO-SUBSTITUTED-2-PYRROLIDINONES AND THEIR UTILITY AS HERBICIDES

This application is a continuation-in-part application of copending application Ser. No. 563,279, now abandoned filed March 28, 1975.

This invention relates to certain novel aromatic N-substituted halo-2-pyrrolidinones (also known as azacyclopentan-3-ones) which are prepared by a novel process and which are useful as herbicides. More specifically, this invention relates to certain monocyclic aromatic or phenyl 2- or N-substituted halo-2-pyrrolidinones, to their preparation and utility of the compounds as herbicides.

The compounds comprising the instant class of compounds correspond to the general formula:

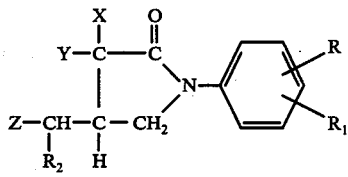

in which X is hydrogen, chlorine or methyl; Y is hydrogen, chlorine or bromine; Z is chlorine or bromine; $R_2$ is alkyl or hydrogen; R is hydrogen, alkyl, acetyl, chlorine, bromine, fluorine, iodine, trifluoromethyl, nitro, cyano, alkoxy, alkylthio, alkylsulfinyl, alkylsulfonyl, trifluoromethylthio, trifluoromethylsulfinyl, trifluoromethylsulfonyl, pentafluoropropionamido, or 3-methylureido; and $R_1$ is hydrogen, alkyl, chlorine or trifluoromethyl.

In the above description, the following preferred embodiments are intended for various substituent groups having alkyl, or an alkyl member as in alkoxy, alkylthio, alkylsulfinyl, or alkylsulfonyl, unless otherwise provided for, those members contain from 1 to 4 carbon atoms, inclusive, in both straight chain and branched chain configurations, for example, methyl, ethyl, n-propyl, isopropyl, n-butyl, isobutyl and the like.

As a consequence of the presence of unsymmetrically substituted carbon centers in certain of the compounds within the scope of this invention, it is recognized that the possibility exists for cis-trans or geometric isomerism. Such cis-trans isomers are stereoisomers whose structures differ only with respect to the arrangement of certain "rigidly" positioned atoms or groups relative to a specified plane of reference. The plane of reference herein is the pyrrolidinone ring. In specifying cis-trans configurations in a monocyclic compound, any of the ring positions having non-identical groups are considered to assign relative configurations. Using the pictoral connotation for representing these relative positions in structural formulas, the pyrrolidinone ring system is considered flat. The atoms or groups under consideration are described as cis when they are on the same side of the plane and trans when they are on opposite sides of the plane (see Gilman's, *Organic Chemistry*, Vol. I, p. 477).

The compounds of this invention have been found to be active herbicides of a general type. That is, members of the class have been found to be herbicidally effective against a wide range of plant species. A method of controlling undesirable vegetation of the present invention comprises applying an herbicidally effective amount of the above-described compounds to the area or plant locus where control is desired.

An herbicide is used herein to mean a compound which controls or modifies the growth of plants. By a "growth controlling amount" is meant an amount of compound which causes a modifying effect upon the growth of plants. Such modifying effects include all deviations from natural development, for example, killing, retardation, defoliation, desiccation, regulation, stunting, tillering, stimulation, dwarfing and the like. By "plants", it is meant germinant seeds, emerging seedlings, and established vegetation, including the roots and above-ground portions.

The intermediates for the preparation of the N-mono cyclic aromatic halo-2-pyrrolidinones are the unsaturated N-alkenyl haloacyl anilides obtained by the acylation of the appropriate unsaturated N-alkenyl anilides. Suitable anilines, that are not commercially available, may be prepared by a number of methods reported in various sources of the chemical literature and various reviews on the subject such as "Synthetic Organic Chemistry" by Wagner and Zook, Chapter 24, John Wiley and Sons, New York, 1961. In the examples to follow, a specific example of the preparation of an intermediate unsaturated N-alkenyl haloacyl anilide is described.

The mono-cyclic aromatic N-substituted halo-2-pyrrolidinones are prepared by several different methods, depending upon the nature of the starting materials and products desired. A preferred method not heretofore disclosed or known in the prior art is the rearrangement reaction of an N-alkenyl containing haloacyl amide in the presence of a catalytic amount of ferrous ion. The use of a solvent is desirable to facilitate processing of the reaction and to aid in the agitation by providing adequate volume, as well as solubilizing the reagents. The preferred solvents include those which are high boiling and which do not interfere with the reaction, for example, diethylene glycol dimethyl ether, dimethyl formamide, dimethyl acetamide, dimethylsulfoxide, mesitylene and the like. Ferrous ion catalyst sources may be provided from various reagents, for example, ferrous chloride, ferrous bromide, iron metal, ferrocene, ferrous acetonyl acetonate and the like.

Since the reaction is a rearrangement of the unsaturated haloacyl amide in the presence of a catalytic amount of ferrous ion, the amounts of reagents is not critical. The reaction is preferably conducted at reflux temperatures. The temperatures for the reaction are best defined between about room temperature and the reflux temperature for the solvent, if one is employed. Preferably, the reaction temperature is between about 50° to about 190° C., more preferably, the temperature range is between about 125° to about 170° C. At the elevated temperatures, the reaction as described hereinabove proceeds rapidly to yield the desired product. In each instance after the reaction is complete, the recovery is carried out by normal work-up procedures, such as crystallization, sublimation, distillation and the like.

Generally, the reaction can be represented by the following equation:

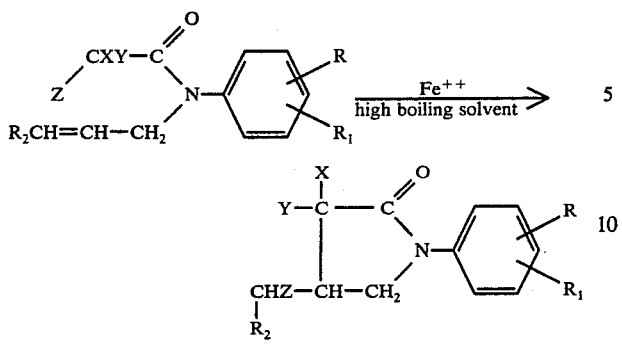

wherein X, Y, Z, R, R₁ and R₂ are defined as above.

The compounds of the present invention and intermediates therefor are more particularly illustrated by the following examples which describe their preparation. Following the examples is a table of compounds which are prepared according to the procedures described herein.

EXAMPLE A

Preparation of Intermediate N-allyl-m-trifluoromethyl aniline from m-trifluoromethyl acetanilide.

N-allyl-m-trifluoromethyl aniline preparation.

m-trifluoromethyl acetanilide was prepared from the aniline by reaction with acetic anhydride. The acetanilide, 192 g., was dissolved in 300 ml. of tetrahydrofuran (THF) and added dropwise with stirring to a slurry of sodium hydride. 24 g., in 200 ml. of THF under a nitrogen atmosphere at ambient temperature. When hydrogen evolution stopped, allylbromide, 121 g. was added and the mixture was allowed to reflux for 1 hour and stir overnight. The mixture was filtered and stripped under vacuum and the residue diluted with methylene chloride, washed with water, dried and stripped under vacuum. Yield was 205 g. of product, N-allyl-m-trifluoromethyl acetanilide. $n_D^{30}$ 1.4532. The product was of sufficient purity to be used in the next step, without further purification.

The product was added to 200 ml. of concentrated hydrochloric acid with 250 ml. of water. The 2-phase system was heated to reflux with stirring until a clear solution resulted in about 2 hours. The mixture was cooled and the product crystallized out. The mixture was treated with 50% sodium hydroxide with cooling to liberate the N-allyl anilide which was extracted with methylene chloride, dried over magnesium sulfate and stripped to give 170 g. of product. Since gas liquid partition chromatography (GLPC) indicated only 85% purity, the material was dissolved in ether and re-precipitated as the hydrochloride with 20% ethereal hydrochloric acid. Yield was 173 g., m.p. 104°–106° C.

N-allyl-m-trifluoromethyl-dichloroacetanilide preparation.

Twenty-three and eight tenths grams of N-allyl-m-trifluoromethyl aniline hydrochloride was suspended in 200 ml. of methylene chloride, 21 g. of triethylamine was added and the mixture stirred in a water bath at room temperature while 15 g. of dichloroacetyl chloride was added dropwise. After stirring about 30 minutes, after addition was complete, the mixture was washed with dilute ~1% sodium hydroxide, dilute ~1% hydrochloric acid and water, separated and dried over magnesium sulfate and the solvent stripped under vacuum. The product was dissolved in ether and treated with 10 g. of 20% ethereal hydrochloric acid, the precipitate filtered off and the ether stripped under vacuum to give 25 g. of product, $n_D^{30}$ 1.4740.

EXAMPLE I

Preparation of N-m-trifluoromethylphenyl-3-chloro-4-chloromethyl-2-pyrrolidinone.

Thirty milliliters of ethylene glycol dimethyl ether (diglyme) was added to 2 g. of ferrous chloride (FeCl₂·4H₂O) and heated to the boiling point under a nitrogen blanket and 10 g. of a water-diglyme mixture was removed. To this was added 12.5 g. of N-allyl-m-trifluoromethyl dichloroacetanilide and heating was continued for 15 minutes at reflux and the conversion to product was determined by GLPC. When conversion was complete (about 30 minutes of reflux), the mixture was cooled, diluted with methylene chloride, washed with 5% hydrochloric acid, separated, dried with magnesium sulfate, treated with activated carbon and Florisil, filtered and the solvent removed under vacuum. Yield was 10 g. of oil, $n_D^{30}$ 1.5032.

As noted above, stereoisomers are possible in the compounds which possess carbon atoms in the pyrrolidinone ring having non-identical groups attached thereto. The compound of this example is one such compound and is used as an example of the separation, identification and later herbicidal activity of the cis and trans configurations.

The compound from the above procedure, an oil, $n_D^{30}$ 1.5032, was allowed to stand overnight and a portion crystallized. This material was triturated with carbon disulfide and a slurry of crystals was obtained. The crystals were removed by filtering the slurry. This was identified by NMR to be the trans configuration (I). m.p. 54°–55° C.

Upon chilling the carbon disulfide filtrate, a further crop of crystals was obtained. After separation and drying, these crystals were identified by NMR to have the cis configuration (II), m.p. 79°–80° C.

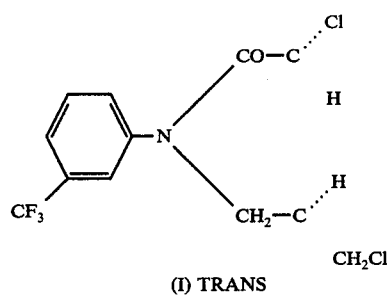

(I) TRANS

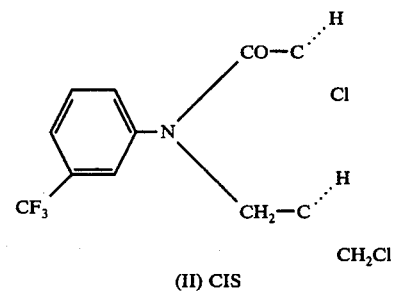

(II) CIS

EXAMPLE II

Preparation of N-m-chlorophenyl-3-chloro-4-chloromethyl-2-pyrrolidinone.

Two grams of $FeCl_2.4H_2O$ was suspended in 30 ml. of diglyme and heated to reflux under a nitrogen atmosphere while 10 g. of water-diglyme mixture were distilled off. N-allyl m-chloro-dichloroacetanilide, 11.1 g., was added and heating continued for 20 minutes and the extent of reaction determined by GLPC. When conversion was complete (20 minutes), the mixture was cooled, diluted with methylene chloride and washed with 5% hydrochloric acid, separated, dried over magnesium sulfate, treated with Florisil and activated carbon, filtered and the solvent stripped under vacuum. The product, a thick dark oil, crystallized on standing and was purified by recrystallization from carbon tetrachloride. Yield was 2.9 g. of product, m.p. 93°-94° C.

EXAMPLE III

Preparation of N-phenyl-3,3-dichloro-4-chloromethyl-2-pyrrolidinone.

One gram of $FeCl_2.4H_2O$ was suspended in 25 ml. of diglyme and 20 g. of N-allyl-trichloroacetanilide was added and the mixture was heated at reflux under nitrogen. After 15 minutes, conversion to product was complete and the mixture was diluted with benzene and washed with water. The product crystallized from benzene solution and was filtered off. A sample was recrystallized from ethanol, giving an m.p. of 133°-134° C.

EXAMPLE IV

Preparation of N-m-trifluoromethylphenyl-3-bromo-4-bromomethyl-2-pyrrolidinone.

One gram of anhydrous ferrous bromide ($FeBr_2$) was suspended in 15 ml. of diglyme, 9.6 g. of N-allyl-m-trifluoromethyl dibromoacetanilide was added and the mixture was heated to reflux under a nitrogen atmosphere for 15 minutes. The mixture was cooled, diluted with methylene chloride, extracted with water and 5% hydrochloric acid solution, dried, treated with florisil, filtered and the solvent stripped under vacuum, Yield was 7.6 g. of a dark liquid.

EXAMPLE V

Preparation of N-m-nitrophenyl-3-chloro-4-chloromethyl-2-pyrrolidinone.

A mixture of 10.1 g. of N-allyl-m-nitro-dichloroacetanilide, 15 ml. of diglyme and 1 g. of anhydrous ferrous chloride ($FeCl_2$) was heated at reflux under nitrogen for 1 hour and cooled. The mixture was diluted with benzene, washed with 5% hydrochloric acid and the solution treated with magnesium sulfate and activated carbon, filtered through a pad of Florisil and the solvent stripped under vacuum. The product, 6 g. of a thick oil, solidified on standing. Trituration with ether gave 3 g. of crystalline solid, m.p. 102°-104° C.

The following is a table of compounds which are prepared according to the aforementioned procedures. Compound numbers have been assigned to them and are used for identification throughout the balance of the specification.

TABLE I

Structure:

$$\begin{array}{c} X \quad O \\ | \quad || \\ Y-C-C \\ | \\ Z-CH-C-CH_2 \\ | \quad | \\ R_2 \quad H \end{array} \quad N - \text{phenyl ring with } R, R_1$$

| Compound No. | X | Y | Z | $R_2$ | R | $R_1$ | m.p. °C. or $n_D^{30}$ |
|---|---|---|---|---|---|---|---|
| 1 | H | Cl | Cl | H | H | H | 85-90 |
| 2 | Cl | Cl | Cl | H | H | H | 133-134 |
| 3 | H | Cl | Cl | H | 2-$CH_3$ | 6-$CH_3$ | semi-solid* |
| 4 | H | Cl | Cl | H | 3-Cl | H | 93-94 |
| 5 | H | Cl | Cl | H | 4-Cl | H | 100-102 |
| 6 | H | Cl | Cl | H | 3-$CF_3$ | H | 1.5032 |
| 7 | $CH_3$ | Cl | Cl | H | H | H | 79-88 |
| 8 | Cl | Cl | Cl | H | 3-Cl | 4-Cl | 119-121 |
| 9 | Cl | Cl | Cl | H | 3-$CF_3$ | H | 100-102 |
| 10 | $CH_3$ | Cl | Cl | H | 3-$CF_3$ | H | 76-78 |
| 11 | H | Cl | Cl | H | 4-$CH_3$ | H | 100-104 |
| 12 | H | Cl | Cl | H | 3-F | H | 60-63 |
| 13 | H | Br | Br | H | 3-$CF_3$ | H | dark liquid* |
| 14 | H | Cl | Cl | H | 3-Cl | 4-Cl | 119-121 |
| 15 | H | Cl | Cl | H | 3-$NO_2$ | H | 102-104 |
| 16 | H | Cl | Cl | H | 3-Cl | 5-Cl | 80-90 |
| 17 | H | Cl | Cl | $CH_3$ | 3-$CF_3$ | H | 1.5020 |
| 18 | H | Cl | Cl | H | 3-CN | H | 1.5550 |
| 19 | Cl | Cl | Cl | H | 3-Cl | 5-Cl | 1.5795 |
| 20 | Cl | Cl | Cl | $CH_3$ | 3-$CF_3$ | H | 1.5122 |
| 21 | Cl | Cl | Cl | H | 3-CN | H | dark red liquid* |
| 22 | H | Cl | Cl | H | 3-$CF_3$ | 4-Cl | 1.5263 |
| 23 | Cl | Cl | Cl | H | 3-$CF_3$ | 4-Cl | 109-112 |
| 24 | H | Cl | Cl | H | 3-$CF_3$S | H | 1.5328 |
| 25 | H | Cl | Cl | H | 3-$CH_3$S | H | 1.5974 |
| 26 | H | Cl | Cl | H | 3-$CF_3$SO | H | 1.5248 |
| 27 | H | Cl | Cl | H | 3-$CH_3$SO | H | 1.5763 |
| 28 | H | Cl | Cl | H | 3-$CH_3SO_2$ | H | glass* |
| 29 | H | Cl | Cl | H | 3-$CF_3SO_2$ | H | 1.5228 |
| 30 | H | Cl | Cl | H | 3-$CF_3$ | 5-$CF_3$ | 1.4690 |
| 31 | H | Cl | Cl | H | 3-$CH_3$O | H | 95-99 |
| 32 | H | Cl | Cl | H | 3-$CH_3$CO | H | 117-121 |
| 33 | H | Cl | Cl | H | 3-$CH_3$ | H | 89-91 |
| 34 | H | H | Cl | H | 3-$CF_3$ | H | 1.4993 |
| 35 | H | Cl | Cl | H | 3-Br | H | 103-105 |
| 36 | H | Cl | Cl | H | 2-Cl | H | 1.5530 |
| 37 | H | Cl | Cl | H | 3-I | H | 107-109 |
| 38 | H | Cl | Cl | H | 4-$CH_3$O | H | 123-125 |
| 39 | H | Cl | Cl | H | 2-$CF_3$ | H | 1.4910 |
| 40 | H | Cl | Cl | H | 3-$C_2F_5$CONH | H | 130-132 |
| 41 | H | Cl | Cl | H | 3-$CH_3$NHCONH | H | 170-172 |
| 42 (cis) | H | Cl | Cl | H | 3-$CF_3$ | H | 79-80 |
| 43 (trans) | H | Cl | Cl | H | 3-$CF_3$ | H | 54-55 |

*=Structure confirmed by infrared analysis.

The foregoing compounds may be designated:
1. 1-phenyl-3-chloro-4-chloromethyl-2-pyrrolidinone
2. 1-phenyl-3,3-dichloro-4-chloromethyl-2-pyrrolidinone
3. 1-(2′,6′-dimethylphenyl)-3-chloro-4-chloromethyl-2-pyrrolidinone
4. 1-m-chlorophenyl-3-chloro-4-chloromethyl-2-pyrrolidinone
5. 1-p-chlorophenyl-3-chloro-4-chloromethyl-2-pyrrolidinone
6. 1-m-trifluoromethylphenyl-3-chloro-4-chloromethyl-2-pyrrolidinone
7. 1-phenyl-3-chloro-3-methyl-4-chloromethyl-2-pyrrolidinone
8. 1(3′,4′-dichlorophenyl)3,3-dichloro-4-chloromethyl-2-pyrrolidinone
9. 1-m-trifluoromethyl-3,3-dichloro-4-chloromethyl-2-pyrrolidinone
10. N-m-trifluoromethylphenyl-3-chloro-3-methyl-3-chloromethyl-2-pyrrolidinone
11. 1-p-tolyl-3-chloro-4-chloromethyl-2-pyrrolidinone 12. 1-m-fluorophenyl-3-chloro-4-chloromethyl-2-pyrrolidinone
13. N-m-trifluoromethyl-3-bromo-4-bromomethyl-2-pyrrolidinone
14. N-3',4'-dichlorophenyl-3-chloro-4-chloromethyl-2-pyrrolidinone
15. N-m-nitrophenyl-3-chloro-4-chloromethyl-2-pyrrolidinone
16. N-3',5'-dichlorophenyl-3-chloro-4-chloromethyl-2-pyrrolidinone
17. N-m-trifluoromethylphenyl-3-chloro-4-(1-chloroethyl)-2-pyrrolidinone
18. N-m-cyanophenyl-3-chloro-4-chloromethyl-2-pyrrollidinone
19. N-3,5-dichlorophenyl-3,3-dichloro-4-chloromethyl-2-pyrrolidinone
20. N-m-trifluoromethylphenyl-3,3-dichloro-4(1-chloroethyl)-2-pyrrolidinone
21. N-m-cyanophenyl-3,3-dichloro-4-chloromethyl-2-pyrrolidinone
22. N-3'-trifluoromethyl-4'-chlorophenyl-3-chloro-4-chloromethyl-2-pyrrolidinone
23. N-3'-trifluoromethyl-4'-chlorophenyl-3,3-dichloro-4-chloromethyl-2-pyrrolidinone
24. N-(m-trifluoromethylthiophenyl)-3-chloro-4-chloromethyl-2-pyrrolidinone
25. N(m-methylthiophenyl)-3-chloro-4-chloromethyl-2-pyrrolidinone
26. N(m-trifluoromethyl sulfinylphenyl)-3-chloro-4-chloromethyl-2-pyrrolidinone
27. N-(m-methylsulfinylphenyl)-3-chloro-4-chloromethyl-2-pyrrolidinone
28. N(m-methylsulfonylphenyl)-3-chloro-4-chloromethyl-2-pyrrolidinone
29. N(m-trifluoromethylsulfonylphenyl)-3-chloro-4-chloromethyl-2-pyrrolidinone
30. N(3',5'-bis-trifluoromethylphenyl)-3-chloro-4-chloromethyl-2-pyrrolidone
31. N-m-methoxyphenyl-3-chloro-4-chloromethyl-2-pyrrolidinone
32. N-m-acetylphenyl-3-chloro-4-chloromethyl-2-pyrrolidinone
33. N-m-tolyl-3-chloro-4-chloromethyl-2-pyrrolidinone
34. N-m-trifluoromethylphenyl-4-chloromethyl-2-pyrrolidinone
35. N-m-bromophenyl-3-chloro-4-chloromethyl-2-pyrrolidinone
36. N-o-chlorophenyl-N-3-chloro-4-chloromethyl-2-pyrrolidinone
37. N-m-iodophenyl-3-chloro-4-chloromethyl-2-pyrrolidinone
38. N-p-methoxyphenyl-3-chloro-4-chloromethyl-2-pyrrolidinone
39. o-trifluoromethyl-3-chloro-4-chloromethyl-2-pyrrolidinone
40. N(m-pentafluoro propionamido phenyl) 3-chloro-4-chloromethyl-2-pyrrolidinone
41. N(m-methylureidophenyl) 3-chloro-4-chloromethyl-2-pyrrolidinone
42. cis 1-m-trifluoromethylphenyl-3-chloro-4-chloromethyl-2-pyrrolidinone
43. trans 1-m-trifluoromethylphenyl-3-chloro-4-chloromethyl-2-pyrrolidinone

HERBICIDAL SCREENING TESTS

As previously mentioned, the herein described compounds produced in the above-described manner are phytotoxic compounds which are useful and valuable in controlling various plant species. Compounds of this invention are tested as herbicides in the following manner.

Pre-emergence Herbicide Screening Test

Using an analytical balance, 20 mg. of the compound to be tested is weighed out on a piece of glassine weighing paper. The paper and compound are placed in a 30 ml. wide-mouth bottle and 3 ml. of acetone containing 1% Tween 20 ® (polyoxyethylene sorbitan monolaurate) is added to dissolve the compound. If the material is not soluble in acetone, another solvent such as water, alcohol or dimethylformamide (DMF) is used instead. When DMF is used, only 0.5 ml. or less is used to dissolve the compound and then another solvent is used to make the volume up to 3 ml. The 3 ml. of solution is sprayed uniformly on the soil contained in a small flat one day after planting weed seeds in the flat of soil. An atomizer is used to apply the spray using compressed air at a pressure of 5 lb./sq. inch. The rate of application is 8 lbs./acre and the spray volume is 143 gallons per acre.

On the day preceding treatment, the flat which is 7 inches long, 5 inches wide and 2.75 inches deep, is filled to a depth of 2 inches with loamy sand soil. Seeds of seven different weed species are planted in individual rows using one species per row across the width of the flat. The seeds are covered with soil so that they are planted at a depth of 0.5 inch. Ample seeds are planted to give about 20 to 50 seedlings per row after emergence depending on the size of the plants.

The seeds used are foxtail (Setaria spp.) — FT; watergrass (*Echinochloa crusgalli*) — WG; red oat (*Avena sativa*) — RO; redroot pigweed (*Amaranthus retroflexus*) — PW; mustard (*Brassica juncea*) — MD; curly dock (*Rumex crispus*) — CD; and hairy crabgrass (*Digitaria sanguinalis*) — CG.

After treatment, the flats are placed in the greenhouse at a temperature of 70° to 85° F. and watered by sprinkling. Two weeks after treatment, the degree of injury or control is determined by comparison with untreated check plants of the same age. The injury rating from 0 to 100% is recorded for each species as per cent control with 0% representing no injury and 100% representing complete kill.

Post-emergence Herbicide Screening Test

Seeds of six plant species, including hairy crabgrass (CG), watergrass (WG), red oat (RO), mustard (MD), curly dock (CD) and Pinto beans (*Phaseolus vulgaris*) (BN), are planted in the flats as described above for pre-emergence screening. The flats are planted in the greenhouse at 70° to 85° F. and watered daily with a sprinkler. About 10 to 14 days after planting when the primary leaves of the bean plants are almost fully expanded and the first trifoliate leaves are just starting to form, the plants are sprayed. The spray is prepared by weighing out 20 mg. of the test compound, dissolving it in 5 ml. of acetone containing 1% Tween 20 ® (polyoxyethylene sorbitan monolaurate) and then adding 5 ml. of water. The solution is sprayed on the foliage using an atomizer at an air pressure of 5 lb./sq. inch. The spray concentration is 0.2% and the rate is 8 lb./acre. The spray volume is 476 gallons per acre.

The results of these tests are shown in Table II.

TABLE II

HERBICIDAL ACTIVITY - SCREENING RESULTS
Per Cent Control at 8 lb./A.

| COMPOUND NUMBER | Pre-emergence | | | | | | | Post-emergence | | | | | |
|---|---|---|---|---|---|---|---|---|---|---|---|---|---|
| | CG | FT | WG | RO | MD | CD | PW | CG | WG | RO | MD | CD | BN |
| 1 | 90 | 80 | 20 | 10 | 100 | 50 | 80 | 100 | 10 | 10 | 80 | 80 | 40 |
| 2 | 100 | 100 | 40 | 0 | 100 | 50 | 80 | 100 | 0 | 0 | 80 | 20 | 0 |
| 3 | 80 | 80 | 80 | 20 | 20 | 10 | 30 | 70 | 60 | 0 | 0 | 0 | 0 |
| 4 | 100 | 100 | 100 | 50 | 100 | 100 | 100 | 100 | 95 | 50 | 100 | 100 | 100 |
| 5*** | 70 | 30 | 0 | 0 | 0 | 0 | 0 | 95 | 0 | 0 | 90 | 40 | 0 |
| 6 | 100 | 100 | 100 | 100 | 100 | 100 | 100 | 100 | 100 | 80 | 100 | 100 | 95 |
| 7 | 90 | 10 | 10 | 0 | 10 | 0 | 0 | 80 | 20 | 0 | 90 | 80 | 60 |
| 8 | 0 | 0 | 0 | 0 | 0 | 0 | 0 | 0 | 0 | 0 | 80 | 0 | 0 |
| 9 | 100 | 100 | 100 | 30 | 100 | 100 | 98 | 90 | 80 | 10 | 100 | 100 | 100 |
| 10 | 100 | 100 | 100 | 0 | 100 | 100 | 100 | 99 | 99 | 10 | 100 | 98 | 100 |
| 11** | 90 | 70 | 0 | 0 | 0 | 0 | 0 | 60 | 0 | 0 | 30 | 50 | 0 |
| 12 | 100 | 100 | 100 | 70 | 100 | 100 | 100 | 100 | 100 | 50 | 100 | 100 | 95 |
| 13 | 90 | 95 | 80 | 10 | 90 | 40 | 90 | 80 | 80 | 20 | 50 | 40 | 100 |
| 14 | 30 | 30 | 0 | 0 | 40 | 40 | 0 | 30 | 20 | 0 | 50 | 0 | 10 |
| 15 | 70 | 98 | 10 | 0 | 30 | 0 | 90 | 70 | 60 | 20 | 100 | 20 | 0 |
| 16 | 90 | 90 | 10 | 0 | 30 | 30 | 90 | 95 | 50 | 10 | 100 | 80 | 80 |
| 17 | 100 | 98 | 60 | 0 | 20 | 0 | 10 | 100 | 50 | 10 | 100 | 70 | 80 |
| 18 | 100 | 100 | 100 | 98 | 100 | 100 | 98 | 100 | 100 | 100 | 100 | 100 | 80 |
| 19 | 10 | 20 | 50 | 10 | 20 | 0 | 0 | 60 | 10 | 10 | 50 | 10 | 0 |
| 20 | 95 | 10 | 60 | 0 | 10 | 0 | 10 | 90 | 20 | 0 | 95 | 50 | 10 |
| 21 | 98 | 98 | 80 | 10 | 80 | 80 | 98 | 100 | 100 | 0 | 100 | 95 | 100 |
| 22 | 100 | 100 | 80 | 30 | 95 | 40 | 95 | 100 | 70 | 90 | 100 | 100 | 100 |
| 23 | 100 | 95 | 40 | 0 | 80 | 30 | 70 | 98 | 60 | 0 | 70 | 80 | 70 |
| 24 | 100 | 100 | 100 | 95 | 98 | 98 | 95 | 100 | 90 | 95 | 100 | 80 | 100 |
| 25 | 100 | 100 | 98 | 10 | 80 | 40 | 70 | 100 | 70 | 10 | 100 | 95 | 80 |
| 26 | 100 | 100 | 100 | 30 | 98 | 98 | 95 | 100 | 70 | 60 | 100 | 100 | 100 |
| 27 | 100 | 95 | 70 | 10 | 80 | 0 | 10 | 100 | 70 | 10 | 100 | 90 | 70 |
| 28 | 100 | 100 | 98 | 10 | 95 | 50 | 10 | 100 | 70 | 20 | 100 | 95 | 80 |
| 29 | 100 | 100 | 70 | 10 | 90 | 60 | 95 | 95 | 50 | 10 | 80 | 80 | 100 |
| 30 | 100 | 100 | 80 | 10 | 80 | 60 | 60 | 100 | 80 | 40 | 80 | 80 | 10 |
| 31 | 100 | 100 | 80 | 0 | 50 | 30 | 95 | 100 | 100 | 10 | 100 | 100 | 100 |
| 32* | 90 | 90 | 0 | 0 | 95 | 40 | 100 | 0 | 0 | 0 | 90 | 10 | 0 |
| 33 | 100 | 100 | 80 | 0 | 60 | 0 | 0 | 100 | 100 | 0 | 100 | 95 | 0 |
| 34 | 100 | 100 | 98 | 0 | 90 | 95 | 98 | 100 | 100 | 10 | 100 | 100 | 100 |
| 35 | 100 | 100 | 100 | 40 | 100 | 100 | 100 | 100 | 100 | 30 | 100 | 100 | 100 |
| 36* | 100 | 100 | 98 | 0 | 98 | 98 | 100 | 100 | 80 | 10 | 100 | 80 | 40 |
| 37 | 100 | 100 | 95 | 10 | 99 | 100 | 100 | 100 | 98 | 70 | 100 | 100 | 100 |
| 38* | 30 | 20 | 0 | 0 | 0 | 0 | 0 | 0 | 0 | 0 | 20 | 0 | 0 |
| 39* | 0 | 0 | 0 | 0 | 0 | 0 | 0 | 10 | 0 | 0 | 30 | 0 | 0 |
| 40 | 100 | 95 | 10 | 0 | 100 | 50 | 98 | 95 | 0 | 0 | 100 | 100 | 0 |
| 41 | 100 | 90 | 70 | 0 | 95 | 95 | 70 | 100 | 20 | 0 | 100 | 100 | 100 |

\* = SCREENING RESULTS - Per cent control at 20 lb/A pre- and post-emergence
\*\* = Pre-emergence Screening Results at 20 lb/A
\*\*\* = Post-emergence Screening Results at 20 lb/A Compounds 42 (cis) and 43 (trans) were bioassayed in the herbicide screen employing the pre-emergence surface technique. The following results in Table III were obtained at 0.25 lb/A, 0.5 lb/A and 1.0 lb/A. A mixture of approximately 40% cis and 60% trans is included for comparison and to show the preferred activity of the cis-configuration.

TABLE III

| COMPOUND/ CONFIGURATION | Rate (lb/A) | CG | FT | WG | WO | PB | AMG | COT | Avg. GR | Avg. BL |
|---|---|---|---|---|---|---|---|---|---|---|
| 42 - cis | 0.25 | 100 | 100 | 80 | 10 | 20 | 40 | 20 | 73 | 27 |
| | 0.5 | 100 | 100 | 99 | 60 | 50 | 30 | 20 | 90 | 33 |
| | 1.0 | 100 | 100 | 100 | 80 | 80 | 70 | 50 | 95 | 67 |
| 43 - trans | 0.25 | 97 | 10 | 20 | 0 | 0 | 0 | 0 | 32 | 0 |
| | 0.5 | 98 | 70 | 40 | 0 | 0 | 0 | 0 | 52 | 0 |
| | 1.0 | 100 | 100 | 80 | 10 | 20 | 0 | 0 | 73 | 7 |
| Mixture (40:60) | 0.25 | 100 | 100 | 60 | 0 | 10 | 0 | 0 | 65 | 3 |
| | 0.5 | 100 | 100 | 90 | 30 | 40 | 20 | 10 | 80 | 23 |
| | 1.0 | 100 | 100 | 100 | 60 | 60 | 50 | 20 | 90 | 43 |

CG, FT, WG and WO = crabgrass, foxtail, watergrass and wild oats
PB, AMG and COT = pinto bean, annual morning glory (*Ipomoea purpurea*), and cotton (*Ipomoea trichocarpa*)

The compounds of the present invention are used as preemergence or post-emergence herbicides and are applied in a variety of ways of various concentrations. In practice, the compounds are formulated with an inert carrier, utilizing methods well known to those skilled in the art, thereby making them suitable for application as dusts, sprays, or drenches and the like, in the form and manner required. The mixtures can be dispersed in water with the aid of a wetting agent or they can be employed in organic liquid compositions, oil and water, water in oil emulsions, with or without the addition of wetting, dispersing or emulsifying agents. An herbicidally effective amount depends upon the nature of the seeds or plants to be controlled and the rate of application varies from 0.10 to approximately 50 pounds per acre. The concentration of a compound of the present invention, constituting an effective amount in the best mode of administration in the utility disclosed, is readily determinable by those skilled in the art.

The phytotoxic compositions of this invention employing an herbicidally effective amount of the compound described herein are applied to the plants in the conventional manner. The present invention contemplates methods of selectively killing, combatting or controlling undesired plants which comprises applying to at least one of (a) such weeds and (b) their habitat, that is, the locus to be protected, an herbicidally effective or toxic amount of the particular active compound alone or together with a carrier or adjuvant. Thus, the dust and liquid compositions can be applied to the plant by the use of power dusters, boom and hand sprayers and spray dusters. The compositions can also e applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles and these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers, pesticides and the like, used as adjuvant or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenoxyacetic acid and the salts, esters and amides thereof; triazine derivatives, such as 2,4-bis(3-methoxypropylamino)-6-methyl-thio-s-triazine; 2-chloro-4-ethylamino-6-isopropylamino-s-triazine, and 2-ethylamino-4-isopropylamino-6-methyl-mercapto-s-triazine, urea derivatives, such as 3-(3,4-dichlorophenyl)-1,1-dimethyl urea and acetamides such as N,N-diallyl-α-chloroacetamide, N-(α-chloroacetyl)-hexamethyleneimine, and N,N-diethyl-α-bromoacetamide, and the like; benzoic acids such as 3-amino-2,5-dichlorobenzoic; and thiocarbamates, such as S-propyl dipropylthiocarbamate; S-ethyldipropylthiocarbamate; S-ethyl hexahydro-1H-azepine-1-carbothioate and the like. Fertilizers useful in combination with the active ingredients include, for example, ammonium nitrate, urea and superphosphate. Other useful additaments include materials in which plant organisms take root and grow, such as compost, manure, humus, sand and the like.

Various changes and modifications are possible without departing from the spirit and scope of the invention described herein and will be apparent to those skilled in the art to which it pertains. It is accordingly intended that the present invention shall only be limited by the scope of the claims.

What is claimed is:

1. A compound having the formula

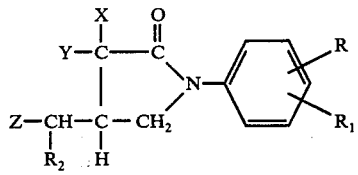

in which X is hydrogen, chlorine or methyl; Y is hydrogen, chlorine or bromine; Z is chlorine or bromine; $R_2$ is alkyl having from 1 to 4 carbon atoms, inclusive, or hydrogen; R is hydrogen, alkyl, acetyl, chlorine, bromine, fluorine, iodine, trifluoromethyl, nitro, cyano, alkoxy having from 1 to 4 carbon atoms, inclusive, alkylthio having from 1 to 4 carbon atoms, inclusive, alkylsulfinyl having from 1 to 4 carbon atoms, inclusive, alkylsulfonyl having from 1 to 4 carbon atoms, inclusive, trifluoromethylthio, trifluoromethylsulfinyl, trifluoromethylsulfonyl, penta fluoropropionamido or 3-methylureido; and $R_1$ is hydrogen, alkyl having from 1 to 4 carbon atoms, inclusive, chlorine or trifluoromethyl.

2. The compound according to claim 1 in which X is hydrogen, Y is chlorine, Z is chlorine, R, $R_1$ and $R_2$ are each hydrogen.

3. The compound according to claim 1 in which X is chlorine, Y is chlorine, Z is chlorine, R, $R_1$ and $R_2$ are each hydrogen.

4. The compound according to claim 1 in which X is methyl, Y is chlorine, Z is chlorine, R, $R_1$ and $R_2$ are each hydrogen.

5. The compound according to claim 1 in which X is hydrogen, Y is chlorine, Z is chlorine, $R_2$ is hydrogen, R is methyl, acetyl, chlorine, bromine, fluorine, iodine, trifluoromethyl, nitro, cyano, trifluoromethylthio, trifluoromethylsulfinyl, trifluoromethylsulfonyl, alkylthio, alkylsulfinyl, alkylsulfonyl, pentafluoropropionamido, or 3-methylureido, and $R_1$ is hydrogen.

6. The compound according to claim 5 in which R is 4-methyl.

7. The compound according to claim 5 in which R is 3-fluorine.

8. The compound according to claim 5 in which R is 3-chlorine.

9. The compound according to claim 5 in which R is 4-chlorine.

10. The compound according to claim 5 in which R is 3-trifluoromethyl.

11. The compound according to claim 5 in which R is 3-nitro.

12. The compound according to claim 5 in which R is 3-cyano.

13. The compound according to claim 5 in which R is 3-trifluorothio.

14. The compound according to claim 5 in which R is 3-trifluorosulfinyl.

15. The compound according to claim 5 in which R is 3-trifluorosulfonyl.

16. The compound according to claim 5 in which R is 3-methylthio.

17. The compound according to claim 5 in which R is 3-methylsulfinyl.

18. The compound according to claim 5 in which R is 3-methylsulfonyl.

19. The compound according to claim 5 in which R is 3-methoxy.

20. The compound according to claim 5 in which R is 3-acetyl.

21. The compound according to claim 5 in which R is 3-methyl.

22. The compound according to claim 5 in which R is 3-bromine.

23. The compound according to claim 5 in which R is 2-chlorine.

24. The compound according to claim 5 in which R is 3-iodine.

25. The compound according to claim 5 in which R is 4-methoxy.

26. The compound according to claim 5 in which R is 2-trifluoromethyl.

27. The compound according to claim 5 in which R is 3-pentafluoropropionamido.

28. The compound according to claim 5 in which R is 3-(3-methylureido).

29. The compound according to claim 5 in which said compound is the cis-isomer configuration.

30. The compound according to claim 29 in which R is 3-trifluoromethyl.

31. The compound according to claim 5 in which said compound is the trans-isomer configuration.

32. The compound according to claim 31 in which R is 3-trifluoromethyl.

33. The compound according to claim 1 in which X is hydrogen, Y is chlorine, Z is chlorine, $R_2$ is hydrogen, R is alkyl and $R_1$ is alkyl.

34. The compound according to claim 33 in which R is 2-methyl and $R_1$ is 6-methyl.

35. The compound according to claim 1 in which X is chlorine, Y is chlorine, Z is chlorine, $R_2$ is hydrogen, R is chlorine, trifluoromethyl or cyano, and $R_1$ is hydrogen or chlorine.

36. The compound according to claim 35 in which R is 3-chlorine, and $R_1$ is 4-chlorine.

37. The compound according to claim 35 in which R is 3-trifluoromethyl and $R_1$ is hydrogen.

38. The compound according to claim 35 in which R is 3-chlorine and $R_1$ is 5-chlorine.

39. The compound according to claim 35 in which R is 3-cyano and $R_1$ is hydrogen.

40. The compound according to claim 35 in which R is 3-trifluoromethyl and $R_1$ is 4-chlorine.

41. The compound according to claim 1 in which X is hydrogen, Y is bromine, Z is bromine, $R_2$ is hydrogen, R is 3-trifluoromethyl and $R_1$ is hydrogen.

42. The compound according to claim 1 in which X is methyl, Y is chlorine, Z is chlorine, $R_2$ is hydrogen, R is 3-trifluoromethyl and $R_1$ is hydrogen.

43. The compound according to claim 1 in which X is hydrogen, Y is chlorine, Z is chlorine, $R_2$ is hydrogen, R is 3-chlorine and $R_1$ is 5-chlorine.

44. The compound according to claim 1 in which X is hydrogen, Y is chlorine, Z is chlorine, $R_2$ is methyl, R is 3-trifluoromethyl and $R_1$ is hydrogen.

45. The compound according to claim 1 in which X is chlorine, Y is chlorine, Z is chlorine, $R_2$ is methyl, R is 3-trifluoromethyl and $R_1$ is hydrogen.

46. The compound according to claim 1 in which X is hydrogen, Y is chlorine, Z is chlorine, R is 3-chlorine and $R_1$ is 4-chlorine.

47. The compound according to claim 1 in which X is hydrogen, Y is chlorine, Z is chlorine, R is 3-trifluoromethyl and $R_1$ is 4-chlorine.

48. The compound according to claim 1 in which X is hydrogen, Y is chlorine, Z is chlorine, R is 3-trifluoromethyl and $R_1$ is 5-trifluoromethyl.

49. The compound according to claim 1 in which X is hydrogen, Y is hydrogen, Z is chlorine, R is methyl, acetyl, chlorine, bromine, fluorine, iodine, trifluoromethyl, nitro, cyano, trifluoromethylthio, trifluoromethylsulfinyl, trifluoromethylsulfonyl, alkylthio, alkylsulfinyl, alkylsulfonyl, pentafluoropropionamido, or 3-methylureido, and $R_1$ and $R_2$ are each hydrogen.

50. The compound according to claim 49 in which R is 3-trifluoromethyl.

51. A method for controlling the growth of undesirable vegetation which comprises applying to at least one of (a) such undesirable vegetation and (b) their habitat, an herbicidally effective amount of a compound having the formula

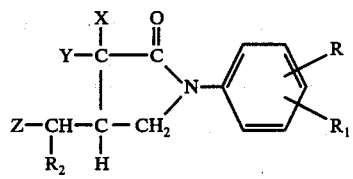

in which X is hydrogen, chlorine or methyl; Y is hydrogen, chlorine or bromine, Z is chlorine or bromine; $R_2$ is alkyl having from 1 to 4 carbon atoms, inclusive, or hydrogen; R is hydrogen, alkyl, acetyl, chlorine, bromine, fluorine, iodine, trifluoromethyl, nitro, cyano, alkoxy having from 1 to 4 carbon atoms, inclusive, alkylthio having from 1 to 4 carbon atoms, inclusive, alkylsulfinyl having from 1 to 4 carbon atoms, inclusive, alkylsulfonyl having from 1 to 4 carbon atoms, inclusive, trifluoromethylthio, trifluoromethylsulfinyl, trifluoromethylsulfonyl, pentafluoroproprionamido, or 3-methylureido; and $R_1$ is hydrogen, alkyl having from 1 to 4 carbon atoms, inclusive, chlorine or trifluoromethyl.

52. The method according to claim 51 in which X is hydrogen, Y is chlorine, Z is chlorine, R, $R_1$ and $R_2$ are each hydrogen.

53. The method according to claim 51 in which X is chlorine, Y is chlorine, Z is chlorine, R, $R_1$ and $R_2$ are each hydrogen.

54. The method according to claim 51 in which X is methyl, Y is chlorine, Z is chlorine, R, $R_1$ and $R_2$ are each hydrogen.

55. The method according to claim 51 in which X is hydrogen, Y is chlorine, Z is chlorine, $R_2$ is hydrogen, R is methyl, acetyl, chlorine, bromine, fluorine, iodine, trifluoromethyl, nitro, cyano, trifluoromethylthio, trifluoromethylsulfinyl, trifluoromethylsulfonyl, alkylthio, alkylsulfinyl, alkylsulfonyl, pentafluoropropionamido, or 3-methylureido; and $R_1$ is hydrogen.

56. The method according to claim 55 in which R is 4-methyl.

57. The method according to claim 55 in which R is 3-fluorine.

58. The method according to claim 55 in which R is 3-chlorine.

59. The method according to claim 55 in which R is 4-chlorine.

60. The method according to claim 55 in which R is 3-trifluoromethyl.

61. The method according to claim 55 in which R is 3-nitro.

62. The method according to claim 55 in which R is 3-cyano.

63. The method according to claim 55 in which R is 3-trifluorothio.

64. The method according to claim 55 in which R is 3-trifluorosulfinyl.

65. The method according to claim 55 in which R is 3-trifluorosulfonyl.

66. The method according to claim 55 in which R is 3-methylthio.

67. The method according to claim 55 in which R is 3-methylsulfinyl.

68. The method according to claim 55 in which R is 3-methylsulfonyl.

69. The method according to claim 55 in which R is 3-methoxy.

70. The method according to claim 55 in which R is 3-acetyl.

71. The method according to claim 55 in which R is 3-methyl.

72. The method according to claim 55 in which R is 3-bromine.

73. The method according to claim 55 in which R is 2-chlorine.

74. The method according to claim 55 in which R is 3-iodine.

75. The method according to claim 55 in which R is 4-methoxy.

76. The method according to claim 55 in which R is 2-trifluoromethyl.

77. The method according to claim 55 in which R is 3-pentafluoropropionamido.

78. The method according to claim 55 in which R is 3-(3-methylureido).

79. The method according to claim 55 in which said compound is the cis-isomer configuration.

80. The method according to claim 79 in which R is 3-trifluoromethyl.

81. The method according to claim 55 in which said compound is the trans-isomer configuration.

82. The method according to claim 81 in which R is 3-trifluoromethyl.

83. The method according to claim 51 in which X is hydrogen, Y is chlorine, Z is chlorine, $R_2$ is hydrogen, R is alkyl and $R_1$ is alkyl.

84. The method according to claim 83 in which R is 2-methyl and $R_1$ is 6-methyl.

85. The method according to claim 51 in which X is chlorine, Y is chlorine, Z is chlorine, $R_2$ is hydrogen, R is chlorine, trifluoromethyl or cyano, and $R_1$ is hydrogen or chlorine.

86. The method according to claim 85 in which R is 3-chlorine, and $R_1$ is 4-chlorine.

87. The method according to claim 85 in which R is 3-trifluoromethyl and $R_1$ is hydrogen.

88. The method according to claim 85 in which R is 3-chlorine and $R_1$ is 5-chlorine.

89. The method according to claim 85 in which R is 3-cyano and $R_1$ is hydrogen.

90. The method according to claim 85 in which R is 3-trifluoromethyl and $R_1$ is 4-chlorine.

91. The method according to claim 51 in which X is hydrogen, Y is bromine, Z is bromine, $R_2$ is hydrogen, R is 3-trifluoromethyl and $R_1$ is hydrogen.

92. The method according to claim 51 in which X is methyl, Y is chlorine, Z is chlorine, $R_2$ is hydrogen, R is 3-trifluoromethyl and $R_1$ is hydrogen.

93. The method according to claim 51 in which X is hydrogen, Y is chlorine, Z is chlorine, $R_2$ is hydrogen, R is 3-chlorine and $R_1$ is 5-chlorine.

94. The method according to claim 51 in which X is hydrogen, Y is chlorine, Z is chlorine, $R_2$ is methyl, R is 3-trifluoromethyl and $R_1$ is hydrogen.

95. The method according to claim 51 in which X is chlorine, Y is chlorine, Z is chlorine, $R_2$ is methyl, R is 3-trifluoromethyl and $R_1$ is hydrogen.

96. The method according to claim 51 in which X is hydrogen, Y is chlorine, Z is chlorine, $R_2$ is hydrogen, R is 3-chlorine and $R_1$ is 4-chlorine.

97. The method according to claim 51 in which X is hydrogen, Y is chlorine, Z is chlorine, $R_2$ is hydrogen, R is 3-trifluoromethyl and $R_1$ is 4-chlorine.

98. The method according to claim 51 in which X is hydrogen, Y is chlorine, Z is chlorine, $R_2$ is hydrogen, R is 3-trifluoromethyl and $R_1$ is 5-trifluoromethyl.

* * * * *